United States Patent [19]
Brauer

[11] Patent Number: 5,951,543
[45] Date of Patent: Sep. 14, 1999

[54] DELIVERY SYSTEM AND METHOD FOR SURGICAL LASER

[75] Inventor: Fritz Brauer, Oceanside, Calif.

[73] Assignee: Clinicon Corporation, Oceanside, Calif.

[21] Appl. No.: 08/885,064

[22] Filed: Jun. 30, 1997

[51] Int. Cl.$^6$ .................................................... A61B 17/36
[52] U.S. Cl. .................................. 606/10; 606/13; 606/17
[58] Field of Search .................................. 606/10, 13, 17, 606/3, 15

[56] References Cited

U.S. PATENT DOCUMENTS

| | | | |
|---|---|---|---|
| 4,126,136 | 11/1978 | Auth, et al. | 128/303.1 |
| 4,469,098 | 9/1984 | Davi | 128/303.1 |
| 4,627,435 | 12/1986 | Hoskin | 128/303.1 |

(List continued on next page.)

FOREIGN PATENT DOCUMENTS

| | | |
|---|---|---|
| 0 368 512 | 5/1990 | European Pat. Off. . |
| 2645354 | 10/1990 | France . |
| 9428783 | 12/1994 | WIPO . |

OTHER PUBLICATIONS

"Myocardial Revascularization by Laser: A Clinical Report", M. Mirhoseini, M.D., et al., *Lasers in Surgery and Medicine*, 3:241–245 (1983).

"Clinical Report: Laser Myocardial Revascularization", Mahmood Mirhoseini, M.D., et al., *Lasers in Surgery and Medicine*, 6:459–461 (1986).

"Drukker Diamond Blades", Dubbeldee Harris Diamond Corp., May 1, 1991.

"One Hundred Consecutive Patients Undergoing Video–Assisted Thoracic Operations", Ralph J. Lewis, M.D. et al., *Annual Meeting of The Society of Thoracic Surgeons*, Feb. 3–5, 1992, 54:421–6.

"Present Role of Thoracoscopy in the Diagnosis and Treatment of Diseases of the Chest", Michael J. Mack, M.D. et al., *Annual Meeting of The Society of Thoracic Surgeons*, Feb. 3–5, 1992, 54:403–9.

"Properties of Diamond", De Beers Industrial Diamond Division, 199.

"Myocardial Revascularization With Laser, Preliminary Findings", O.H. Frazier, MD et al., *Circulation*, 1995; 92[suppl II]:II–58–II–65.

"Quantification of Mitral Valve Stenosis by Three–Dimensional Transesophageal Echocardiagraphy", Iri Kupferwasser et al., *International Journal of Cardiac Imaging* 12:241–0247, 1996, Kluwer Academic Publishers.

"Cardio Genesis Corporation—Prospectus", Bear, Stearns & Co. Inc., Montgomery Securities, Piper Jaffray Inc., May 21, 1996.

(List continued on next page.)

*Primary Examiner*—Michael Buiz
*Assistant Examiner*—Julian W. Woo
*Attorney, Agent, or Firm*—Brown, Martin, Haller & McClain

[57] ABSTRACT

The system and method of delivery of laser radiation comprises a flexible hollow waveguide connectable at a first end to a low power laser source, such as a $CO_2$ laser, a rigid hollow waveguide having a proximal end and a distal end, a coupler for coupling the second end of the flexible hollow waveguide to the proximal end of the rigid hollow waveguide and a diamond tip partially disposed within and extending from the distal end of the rigid waveguide. The diamond tip has an entrance face for receiving laser radiation and at least one exit face for transmitting laser radiation toward an area of biological tissue. The exit end of the diamond tip may be flat, parallel to the entrance face, curved, to act as a lens providing a focusing function, or beveled, to create one or more blade edges to limit the point(s) of exit of the laser radiation and to provide a cutting edge which may be used in combination with the radiation to simultaneously create and photocoagulate the tissue at an incision.

24 Claims, 5 Drawing Sheets

U.S. PATENT DOCUMENTS

| | | | |
|---|---|---|---|
| 4,658,817 | 4/1987 | Hardy | 128/303.1 |
| 4,686,979 | 8/1987 | Gruen et al. . | |
| 4,693,244 | 9/1987 | Daikuzono | 128/303.1 |
| 4,761,056 | 8/1988 | Evans, et al. | 350/174 |
| 4,877,307 | 10/1989 | Kalmanash | 350/132 |
| 4,917,083 | 4/1990 | Harrington, et al. | 606/15 |
| 4,927,231 | 5/1990 | Levatter | 350/96.32 |
| 4,993,412 | 2/1991 | Murphy-Chutorian | 606/7 |
| 5,005,944 | 4/1991 | Laakmann, et al. | 350/96.32 |
| 5,020,880 | 6/1991 | Bluege | 350/319 |
| 5,044,717 | 9/1991 | Levatter | 385/33 |
| 5,071,222 | 12/1991 | Laakmann, et al. | 385/125 |
| 5,097,525 | 3/1992 | Garcia, et al. | 385/75 |
| 5,114,403 | 5/1992 | Clarke, et al. | 604/96 |
| 5,125,926 | 6/1992 | Rudko, et al. | 606/19 |
| 5,176,675 | 1/1993 | Watson, et al. | 606/15 |
| 5,194,712 | 3/1993 | Jones | 219/121.67 |
| 5,207,673 | 5/1993 | Ebling, et al. | 606/16 |
| 5,222,174 | 6/1993 | Miles | 385/118 |
| 5,245,189 | 9/1993 | Satoh, et al. | 250/343 |
| 5,273,788 | 12/1993 | Yu | 427/544 |
| 5,280,378 | 1/1994 | Lombardo | 359/199 |
| 5,304,167 | 4/1994 | Freiberg | 606/3 |
| 5,320,620 | 6/1994 | Long, et al. | 606/28 |
| 5,335,245 | 8/1994 | Marie, et al. | 372/103 |
| 5,376,099 | 12/1994 | Ellis, et al. | 606/166 |
| 5,380,316 | 1/1995 | Aita, et al. | 606/7 |
| 5,389,096 | 2/1995 | Aita, et al. | 606/15 |
| 5,423,840 | 6/1995 | Casebeer, et al. | 606/166 |
| 5,440,664 | 8/1995 | Harrington, et al. | 385/125 |
| 5,480,050 | 1/1996 | Morrow et al. . | |
| 5,495,541 | 2/1996 | Murray, et al. | 385/33 |
| 5,497,441 | 3/1996 | Croitoru, et al. | 385/125 |
| 5,505,725 | 4/1996 | Samson | 606/7 |
| 5,530,780 | 6/1996 | Ohsawa | 385/31 |
| 5,532,852 | 7/1996 | Kalmanash | 359/73 |
| 5,536,234 | 7/1996 | Newman | 600/104 |
| 5,554,152 | 9/1996 | Aita, et al. | 606/7 |
| 5,558,668 | 9/1996 | Landkford, et al. | 606/14 |
| 5,567,471 | 10/1996 | Harrington, et al. | 427/163.2 |
| 5,591,157 | 1/1997 | Hennings, et al. | 606/3 |
| 5,591,159 | 1/1997 | Taheri | 606/15 |
| 5,607,421 | 3/1997 | Jeevanandam, et al. | 606/15 |
| 5,658,275 | 8/1997 | Saadat | 606/17 |

OTHER PUBLICATIONS

"Long– and Short–Term Effects of Transmyocardial Laser Revascularization in Acute Myocardial Ischemia", K.A. Kadipasaoglu, Ph.D. et al., *Lasers in Surgery and Medicine* 20:6–14 (1997).

"TMR Becomes an Option for Heart Patients", Individual Inc., 1997.

"Jungle 2 City: A Slice of Life", Rex Dalton, *The San Diego Union–Tribune,* Apr. 16, 1997.

"Saving the Whole with a Smaller Hole", Rex Dalton, *The San Diego Union–Tribune,* Apr. 16, 1997.

"Advanced Diamond Products", Drukker International BV.

"Diafilm", De Beers Industrial Diamond Division.

"A Diamond in Miniature", D. Drukker & SN, N.V.

DELIVERY SYSTEM AND METHOD FOR SURGICAL LASER

BACKGROUND OF THE INVENTION

1. Field of the Invention

The present invention relates to an instrument for transmitting laser radiation for application to biological tissue for removal, penetration or treatment of the tissue and more particularly to an instrument for efficiently and accurately delivering laser radiation to a predetermined location on the biological tissue.

2. Description of Related Art

Surgical applications of lasers are well established in opthalmology, otolaryngology, gynecology, dermatology and plastic surgery, having been in use, in some cases, for over two decades. Lasers have also become well accepted in the treatment of cardiovascular diseases. The types of lasers are nearly as numerous as the procedures that use them, and selection of a laser for any given procedure depends upon the laser-tissue interaction, which phenomena have been widely reported, and the desired outcome of that interaction. See, e.g., M. J. C. van Gemert and A. J. Welch, "Time Constants in Thermal Laser Medicine", *Lasers in Surgery and Medicine* 9:405–421 (1989); and J. L. Ratz, "Laser Physics", *Clinics in Dermatology* 13:11–20 (1995), which are incorporated herein by reference. The types of lasers may be grouped into ultraviolet (193–351 nm), visible wavelength (400–700 nm), and infrared (700–100,000 nm). The visible light lasers, such as argon (488–514 nm), flashlamp-pumped dye (510 nm), copper vapor (578 nm) and ruby (694 nm), are commonly used for selective photothermalysis, e.g., photocoagulation of vascular and pigmented lesions. Laser light within the visible range can be delivered using a number of conventional optical techniques including refractive lenses and quartz fiber optics. Examples of visible light delivery systems are provided in U.S. Pat. No. 5,207,673 of Ebling, et al., "Fiber Optic Apparatus for Use with Medical Lasers", No. 5,495,541 of Murray, et al., "Optical Delivery Device with High Numerical Aperture Curved Waveguide", and No. 5,530,780 of Ohsawa, "Fiber Optic Laser Conducting and Diffusion Device", the disclosures of which are incorporated herein by reference. Ultraviolet (UV) lasers, or excimer lasers, which include argon-fluoride (193 nm) and krypton-fluoride (248 nm), have been used predominantly in photorefractive keratectomy to ablate corneal tissue. Excimer lasers have also been reported for ablation of skin. (See, e.g., R. J. Lane, et al., "Ultraviolet-Laser Ablation of Skin", *Arch. Dermatol.—* 121: 609–617 (May 1985).)

Visible, UV and near IR laser light have been combined with surgical tips to provide precise control of application of laser radiation and/or to provide means for coagulating blood adjacent an incision. U.S. Pat. No. 4,126,136 of Auth, et al., describes a transparent scalpel blade connected to a fiber optic waveguide which transports laser radiation to the blade. The blade, which is preferably synthetic sapphire ($Al_2O_3$), emits laser radiation through the tapered cutting edge to photocoagulate the blood. U.S. Pat. No. 4,627,435 of Hoskin discloses a surgical knife formed from a diamond blade optically coupled to a Nd:YAG laser by a fiber optic bundle. The diamond blade is heated by the laser radiation to provide a cauterizing action while making the incision. The diamond blade may also be coupled to a visible laser to provide illumination for enhanced visibility of the incision site. U.S. Pat. No. 4,693,244 of Daikuzono describes an artificial sapphire tip coupled to a quartz optical fiber to transmit radiation from a Nd:YAG laser. The sapphire tip is heated by the radiation to coagulate the blood at an incision made with a separate surgical blade. U.S. Pat. No. 5,320,620 of Long, et al., describes a laser surgical device with a blunt light emitting element for coagulation. The tip, which may be sapphire, silica or YAG, is coupled to an optical fiber for receiving laser energy. The tip may be coated with a high melting point material to absorb the radiation and heat the tip. The disclosures of each of the above patents, and all other patents cited in this specification, are incorporated herein by reference. U.S. Pat. No. 5,194,712 of Jones describes a single crystal diamond cutting tool with an anti-reflection coating bonded to the entry and exit faces of the cutting tool to provide efficient transfer of laser light, or to concentrate laser light at the desired incision.

Of the infrared lasers, which include $CO_2$ (10.6 micron) and Nd:YAG (neodymium:yttrium-aluminum-garnet) (1.06 micron), the $CO_2$ laser is most widely used for surgical applications of ablation and cutting of tissue. It is also more readily available and more economical, costing much less than other types of surgical lasers. While Ho:YAG and Nd:YAG lasers still emit light at a short enough wavelength that conventional optical delivery techniques can be used, because of its position in the far-infrared region of the electromagnetic spectrum, the $CO_2$ laser cannot be delivered through quartz fiber optics, or silica or sapphire lenses, since these materials are opaque to the 10 micron wavelength and absorb the infrared laser radiation. (Materials that are commonly used with $CO_2$ laser light, both as lenses and as mirrors, include sodium chloride, potassium chloride, zinc selenide, and germanium.) The $CO_2$ laser light is typically directed through a series of mirrors in a complex articulating system through which the light is delivered to a handpiece containing a lens which will allow the beam to be focussed in a non-contact manner onto the target location. Examples of delivery optics for $CO_2$ laser radiation are disclosed in U.S. Pat. No. 5,497,441 of Croitoru, et al., "Hollow Waveguide Tips for Controlling Beam divergence and Method of Making Such Tips"; No. 5,005,944 of Laakmann, et al., "Hollow Lightpipe and Lightpipe Tip Using a Low Refractive Index Inner Layer"; and No. 4,917,083 of Harrington, et al., "Delivery System for a Laser Medical System." Relatively recent developments in waveguide technology include a flexible hollow waveguide which is suitable for use with $CO_2$ lasers having powers over 80 W. Such waveguides are disclosed in U.S. Pat. Nos. 5,440,664 and 5,567,471 of Harrington, et al.

It is known that single crystal type II diamond (pure carbon, effectively free of nitrogen impurity) has very low absorption at 10.6 microns, on the order of 0.03 $cm^{-1}$, and also has high thermal conductivity, on the order of 2,000 W/m/K in comparison with other far-IR transmitting materials. High quality synthetic diamonds, including diamond films formed using chemical vapor deposition (CVD) have been made possessing similar mechanical, optical and thermal characteristics. For this reason laser cavity windows formed from diamond have been described for use in high power lasers, particularly $CO_2$ lasers. See, e.g., U.S. Pat. No. 5,335,245 of Marie, et al.; and U.S. Pat. No. 5,245,189 of Satoh, et al. See, also, U.S. Pat. No. 5,194,712 of Jones, supra with regard to use of diamond for transmission of laser radiation, including that from a $CO_2$ laser.

In recent years significant attention has been focused on the application of lasers to treating cardiovascular diseases, in particular, techniques for revascularization of ischemic myocardium. The procedure, laser transmyocardial revascularization (TMR), was first reported in the early 1980's following procedures which used a $CO_2$ laser to form channels in damaged heart tissue to increase myocardial perfusion via the transport of oxygenated blood through the channels. (See, e.g., M. Mirhoseini, et al., "Myocardial Revascularization by Laser: A Clinical Report", *Lasers in Surgery and Medicine* 3:241–245 (1983).) This initial work was performed on an arrested heart using a low power (80 W) $CO_2$ laser. Subsequent work in TMR led to the numerous laser systems which could be used on a beating heart, such as the one disclosed in U.S. Pat. No. 4,658,817 of Hardy ("Method and Apparatus for Transmyocardial Revascularization Using a Laser"), in which a $CO_2$ laser was used. U.S. Pat. Nos. 5,380,316, and 5,554,152, of Aita, et al., assigned to CardioGenesys Corporation of Santa Clara, Calif., disclose the use of a $CO_2$ laser or a Holmium:YAG laser for TMR procedures, however, the commercial system actually marketed by CardioGenesys is based upon a Ho:YAG laser with a fiber optic/lens contact-type delivery system. The wavelength emitted by the Ho:YAG laser, 2.1 microns, like the Nd:YAG, is sufficiently short to permit use of conventional optical delivery techniques, eliminating the delivery limitations experienced with $CO_2$ lasers. U.S. Pat. No. 5,607,421 of Jeevanandam, et al., describes a laser TMR system which uses a thulium-holmium-chromium:YAG laser (THC:YAG) laser with conventional optical fiber delivery via a catheter passed through the left atrium.

Development of other laser TMR systems for investigational use has been reported by PLC Systems, Inc., of Franklin, Mass., Eclipse Surgical Technologies, Inc., of Sunnyvale, Calif., and Helionetics, Inc., of Van Nuys, Calif., all for use on a beating heart. The Eclipse TMR system uses a Ho:YAG laser with a fiber optic handpiece for contact delivery to the myocardium. The Helionetics system is based an excimer laser and uses conventional fiber optic delivery techniques. PLC Systems uses a high power (1000 Watt) $CO_2$ laser in its Heart Laser™ with an articulated arm delivery system, such as that described in U.S. Pat. No. 5,558,668 of Lankford, et al., assigned to PLC Medical Systems, Inc.

Primary distinctions between the use of Ho:YAG or excimer lasers and $CO_2$ lasers include that the $CO_2$ lasers can create a transmural channel with a single pulse synchronized with the R wave (beginning of contraction) of a beating heart. (An exemplary synchronization system is disclosed in U.S. Pat. No. 5,125,926 of Rudko, et al.) The Ho:YAG and excimer lasers utilize low pulse energy and must fire multiple pulses over multiple cardiac cycles, typically without synchronization, in order to form a single channel. Another important distinction is in the delivery systems, with $CO_2$ based systems using articulated arms, supplying the laser energy in a non-contact manner, thus requiring higher power laser sources and more invasive access methods, e.g., open chest surgery. Distinctions also lie in the relative costs and reliability of $CO_2$ and excimer laser-based systems: $CO_2$ lasers are relatively readily available, inexpensive and easily maintained, and many hospitals already possess or have access to such lasers. Excimer lasers are large, expensive, and difficult to maintain, requiring frequent service, and use highly toxic gas as the lasing medium.

The precision required for safe and controllable formation of multiple small diameter channels in the myocardium suggests that a contact or near-contact methods for application of laser energy would be preferred. Further, the ability to utilize contact delivery methods enables the use of less invasive procedures for obtaining access to the heart, e.g., small incisions between the ribs (thoracotomy) as opposed to open chest surgery. However, according to TMR techniques currently in use, the advantages of contact delivery must be offset by the lower ablative energy provided by shorter wavelength (mid- or near-IR) light.

In view of the above-identified deficiencies in the TMR prior art, there remains a need for a system and method for delivering laser radiation, especially radiation from a $CO_2$ laser, in a precisely controlled manner as required for delicate surgical procedures. The delivery system and method disclosed in the following written description and drawings addresses and overcomes each of these deficiencies as well as providing other effective laser surgery techniques.

SUMMARY OF THE INVENTION

It is an advantage of the present invention to provide a laser delivery system and method which permits precise control of the location of impingement of laser radiation on biological tissue in both contact and non-contact applications.

It is another advantage of the present invention to provide means for combining optical and mechanical means for ablation/incision of biological tissue.

Still another advantage of the present invention is to provide a system and method for performing transmyocardial revascularization using a low power $CO_2$ laser.

Yet another advantage of the present invention is to provide a delivery system for inexpensively retrofitting an existing $CO_2$ laser system for performing $CO_2$ laser surgery at low power levels.

Another advantage of the present invention is to provide a system and method for performing left ventricular remodeling procedures using a combination of laser and mechanical surgical devices.

Still another advantage of the present invention is to provide a system and method for performing laser myringotomy with improved patency.

In an exemplary embodiment, the system and method of delivery of laser radiation comprises a flexible hollow waveguide connectable at a first end to a low power $CO_2$ laser source, a rigid hollow waveguide having a proximal end and a distal end, a coupler for coupling the second end of the flexible hollow waveguide to the proximal end of the rigid hollow waveguide and a diamond tip partially disposed within and extending from the distal end of the rigid waveguide. The diamond tip has an entrance face for receiving laser radiation and at least one exit face for transmitting laser radiation toward a target area of biological tissue. Means are provided for controlling the rigid hollow waveguide to direct movement of the diamond tip and the laser light emitted therefrom.

The rigid hollow waveguide is a stainless steel tube with an inner diameter and a smooth, polished internal surface for reflection of the laser radiation. Other materials which meet the reflective and heat absorptive requirements for transmitting the laser radiation may be substituted for the stainless steel. The entrance end of the diamond tip has an outer diameter to closely fit within the inner diameter of the rigid waveguide, where it is brazed, glued or otherwise firmly affixed. The exit end of the diamond tip may be flat, parallel to the entrance face, curved, to act as a lens providing a focusing function, or beveled, to create one or more blade edges to limit the point(s) of exit of the laser radiation and to provide a cutting edge which may be used in combination with the radiation to simultaneously create and cauterize an incision. The diameter and emission location of the radiation leaving the diamond tip are controlled by polishing only the desired exit area of the exit face, leaving the remainder of the diamond with a roughened or "frosted" surface which will reflect the majority of laser radiation back into the body of the diamond so that it can be re-directed out of the exit face. Alternatively, for more efficient internal reflection, the areas of the diamond tip through which no radiation should escape may be bonded with a metal or ceramic coating which reflects the laser light.

The combination of the flexible waveguide, coupler, rigid hollow waveguide and diamond tip may be used for formation of channels in a transmyocardial revascularization (TMR) procedure. Using a low power $CO_2$ laser (under 1000 Watts, preferably less than 100 W) emitting at 10.6 microns coupled via a flexible waveguide to a rigid waveguide/diamond tip assembly, the distal end of the assembly is guided to an area of the heart to be revascularized. The diamond tip is preferably configured as a flat window or a slightly curved lens, i.e., a lens having a relatively long focal point which will not significantly modify the beam diameter or power density at close range. Placement of the diamond tip at the desired location may be by catheter through one of the patient's major vessels, so that the ablation begins on the interior of the beating heart, or through a small incision in the chest wall, with the laser radiation being introduced outside-in, through the exterior (epicardial) portion. The diamond tip is placed in direct contact with the tissue of the beating heart for delivery of ablative laser radiation for formation of a channel. The tip is advanced as the ablation proceeds to control the depth of the channel. In order to avoid arrhythmogenesis, it is preferred that the laser pulses be synchronized to the peak of the R-wave of the patient's ECG.

Monitoring of the TMR procedure is achieved using a three-dimensional image acquisition endoscope with a head-mounted display. This may be supplemented using an ultrasonic imaging endoscope inserted into the patient's esophagus, as is known in the art. Conventional heart rate monitoring techniques may be used to generate a trigger signal to synchronize delivery of the laser radiation with the heart beat.

A similar delivery system in combination with a low power $CO_2$ laser may be used for performing left ventricular remodeling, a surgical procedure for severe dilated cardiomyopathy in which a section of the enlarged left ventricle is surgically removed to reduce the size of the heart and to increase pumping function. A variation from the TMR embodiment, the diamond tip is formed as a blade which is frosted or otherwise treated to minimize escape of laser radiation everywhere except at the cutting edge. The cutting edge in combination with the laser radiation allows the simultaneous cutting of the heart tissue and photocoagulation of blood along the incision.

Treatment of otitis media by perforation of the eardrum (myringotomy) can be achieved by combining the delivery system as described for TMR with an otoscope to permit viewing of the tympanic membrane to properly position the perforation. Using a low power laser with the diamond tip held a short distance from, but not in contact with the membrane, an area of the tissue is denatured. Using a diamond tip shaped as a lance, or a diamond lens for focusing the laser to a small point, a small area of the denatured tissue is then punctured to provide a vent for pressure behind the eardrum. The puncturing is achieved by ablation, cutting, or a combination of both. After the pressure has been reduced, a larger perforation is made through the denatured tissue, leaving a rim of necrosis to delay healing of the perforation to provide improved patency, thus permitting the draining of fluids from the middle ear without requiring placement of a drainage tube.

BRIEF DESCRIPTION OF THE DRAWINGS

Understanding the present invention will be facilitated by consideration of the following detailed description of preferred embodiments of the present invention taken in conjunction with the accompanying drawings, in which like numerals refer to like parts and in which:

FIG. 3a shows a blade having one beveled edge, FIGS. 3b and 3c show alternate configurations of blades having two beveled edges, and FIG. 3d shows a blade having four beveled edges;

FIG. 6a shows initial placement of the diamond tip, FIG. 6b shows a channel partially formed in the myocardium, FIG. 6c shows a completed channel and FIG. 6d shows a plurality of completed channels and a partially completed channel;

FIG. 7a shows formation of the incision around the wedge of tissue to be excised, and FIG. 7b shows the heart after completion of the procedure;

FIG. 8a shows the first step of denaturing the tissue and FIG. 8b shows the second step of perforating the tympanic membrane within the denatured area.

DETAILED DESCRIPTION OF THE PREFERRED EMBODIMENT

Figure 1:
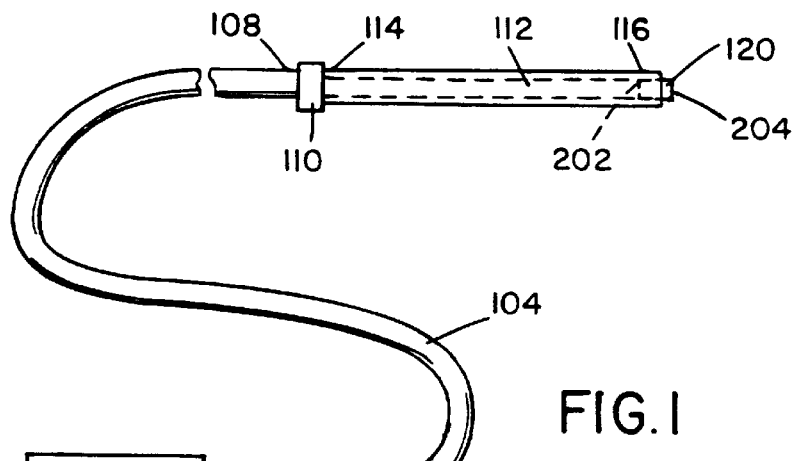
FIG. 1 is a diagrammatic view of the laser delivery system of the present invention.

As illustrated in FIG. 1, a surgical laser radiation delivery system for use with a low power laser source 102 comprises a flexible hollow waveguide 104 connectable at a first end 106 to laser source 102, a rigid hollow waveguide 112 having a proximal end 114 and a distal end 116, a coupler 110 for coupling the second end 108 of flexible hollow waveguide 104 to the proximal end 114 of rigid hollow waveguide 112 and a diamond tip 120 partially disposed within and extending from distal end 116 of rigid waveguide 112. As can be seen in more detail in FIG. 2, diamond tip 120 has an entrance face 202 for receiving laser radiation and at least one exit 204 face for transmitting laser radiation toward an area of biological tissue 100. The rigid hollow waveguide 112 may include means for gripping in the user's hand to support and direct movement of the diamond tip 120 and the laser light emitted therefrom, or may be combined with a steerable endoscope to enable guidance.

Flexible waveguide 104 is preferably be constructed according to the disclosure of Harrington, et al. in U.S. Pat. No. 5,567,471, which is incorporated herein by reference. The waveguide of Harrington, et al. comprises a hollow tube of flexible, thin-wall silica-glass tube with a protective sheath on its outer surface. The inner surface of the tube is coated with a material that is optically reflective at mid-infrared wavelengths, such as silver, so that the coating is optically smooth. A dielectric film, such as silver iodide, is deposited on the reflective layer.

The rigid hollow waveguide 112 is a stainless steel tube with an inner diameter and a smooth, polished internal surface for reflection of the laser radiation. The inner diameter of waveguide 112 is preferably on the order of 1.0 to 1.5 mm or less to provide greater control over the spatial profile of the output laser beam. The outer diameter is determined primarily by the materials used, to assure that the tube can be formed with a smooth internal surface without irregularities form creases or wrinkles which might disrupt the efficient transfer of laser energy. The outer diameter may also depend on any requirements for housing waveguide 112 within some other structure, such as a catheter. Other materials which meet the reflective and heat absorptive requirements for transmitting the laser radiation may be substituted for the stainless steel. Such materials include invar, nickel, platinum, and other high specific heat metals or alloys.

Figure 2:
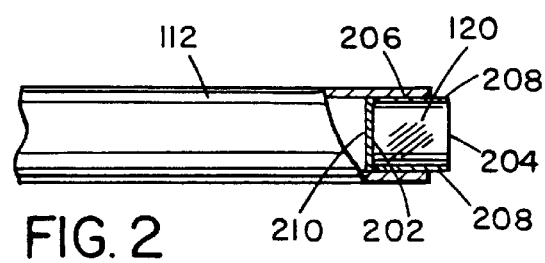
FIG. 2 is a side elevation, partially cut away, showing the rigid waveguide and diamond tip of a first embodiment of the delivery system.

The entrance face 202 of the diamond tip 120 has an outer diameter to closely fit within the inner diameter of the rigid waveguide, i.e., on the order of 1.0 to 1.5 mm or less, where it is brazed, glued or otherwise firmly affixed, for example, by crimping the end of waveguide 112 around the tip 120. The surface of entrance face 202 is preferably flat, perpendicular to the axis of waveguide 112, and may be coated or bonded with an anti-reflective coating 210 such as silicon nitride or silicon carbide, as disclosed in U.S. Pat. No. 5,194,712 of Jones. The exit face 204 of the diamond tip 120 may be flat, parallel to entrance face 202, as shown in FIG. 2, curved, to act as a lens providing a focusing or beam expanding function, or beveled, as shown in FIGS. 3a–3d, to create one or more blade edges to limit the point(s) of exit of the laser radiation and to provide a cutting edge which may be used in combination with the radiation to simultaneously optically and mechanically cut and induce photocoagulation as the incision is made. (Note that, for purposes of this description, the phrase "mechanically cut" means the cutting performed using a sharp blade pressed against the tissue, while "optically cut" means removal or separation of tissue by laser ablation, regardless of whether the laser radiation is applied in a contact or non-contact manner.)

Figures 3A, 3B, 3C, 3D:
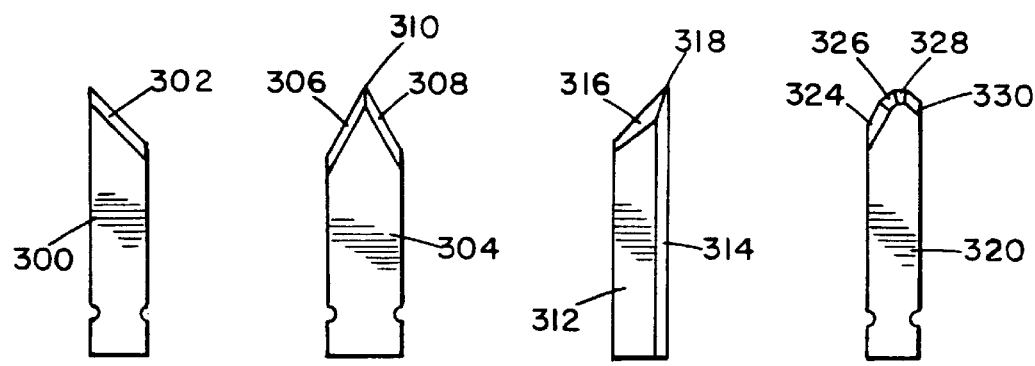
FIGS. 3a–3d are diagrammatic views of alternative embodiments of diamond tips for use in the delivery system of the present invention, where

As in conventional diamond surgical blades for mechanical cutting, multiple facets may be created to form, for example, a spear tip (using two facets), a triple edge (using three facets), or a curved tip (with four or more facets to approximate a rounded blade). FIG. 3a shows a blade 300 with a single beveled edge 302. In this configuration, laser radiation would be emitted only through beveled edge 302, which is also the only cutting edge. FIG. 3b illustrates a blade 304 with two beveled edges 306,308 to form a lance or spear. Both edges 306,308 can be used to cut, and apex 310 can be used to pierce. Laser radiation will be emitted through both beveled edges 306,308. FIG. 3c shows an alternate two-edge blade 312 with beveled edges 314,316. Edge 314 is long and may be used for larger-area slicing, with apex 318 for piercing. FIG. 3d illustrates a curved blade 320 with four beveled edges 324,326,328,330 formed at the distal end of the blade.

Figure 4A:
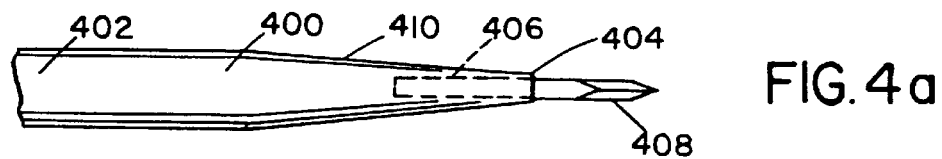
FIGS. 4a and 4b are diagrammatic views of an alternative embodiment of the rigid waveguide, with FIG. 4a being a side elevational view and FIG. 4b being a top view.
Figure 4B:
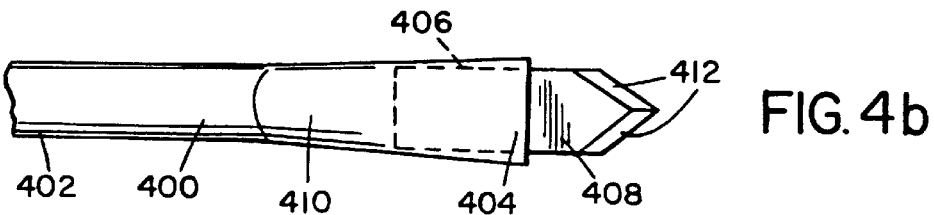

The diameter and emission location of the radiation leaving the diamond tip may be further controlled by polishing only the desired area of the exit face, leaving the remainder of the diamond with a roughened or "frosted" surface which will reflect the majority of laser radiation back into the diamond so that it can be re-directed out of the exit face. Alternatively, for more efficient internal reflection, the areas of the diamond tip through which no radiation should escape may be bonded or coated with a metal or ceramic film. In the embodiment of FIG. 2, the sidewalls 206 of diamond tip 120 are treated with internally reflective coating 208 to minimize escape of laser radiation. In FIGS. 3a–d, all areas but the beveled edges may be treated to enhance internal reflection and guide the laser radiation toward edge. The beveled edges are formed in accordance with conventional techniques for forming surgical diamond cutting blades, in which a facet is formed at the cutting edge. The dimensions of such surgical blades are generally appropriate for use in combination with the inventive laser system. For example, the base end of a commercially-available surgical blade manufactured by the Drukker Group (D. Drukker & Zn, N.V., Amsterdam, The Netherlands) may have a width in the range of 0.7 to 1.4 mm and a thickness of 0.17 mm, such that it would easily fit within the interior of the hollow waveguide 112. It may be preferable to form the base end of the blade to have an entrance face with a shape and an area the just fits within the cross-sectional shape and area of the hollow waveguide to enhance efficiency in capture of the laser radiation incident upon the entrance face and to minimize diffraction losses where the laser radiation impinges upon a corner or edge of the entrance face. Thus, if the hollow waveguide is rounded, the entrance face is preferably rounded. Since it may be easier to form the base of a diamond blade with a rectangular or square cross-section, the hollow waveguide may be crimped or otherwise modified to create a corresponding rectangular or square cross-section at its interior with approximately the same cross-sectional area as the base of the blade. Commercial diamond blades can range from 0.25 mm down to less than 35 microns in thickness with widths on the order of 1 mm or less. A modification for accommodating an exemplary commercial diamond blade is illustrated in FIGS. 4a and 4b, showing a hollow waveguide 400 with a circular cross-section at proximal end 402 and a rectangular cross-section at distal end 404 to match the rectangular shape of the base 406 of diamond blade 408. The transition 410 from circular to rectangular cross-section is made as gradual as possible to retain the smooth internal surface to minimize scattering loss and mode conversion. With the laser radiation being emitted only from beveled edge(s) 412, the edge can simultaneously cut the tissue and coagulate the blood at the incision.

The diamond tip is preferably formed using a single crystal natural diamond, which, ideally, is a type IIa diamond. Type IIa diamonds are effectively free from nitrogen impurities and have enhanced optical and thermal properties. Other types of diamonds may be used as long as they possess the thermal and optical characteristics required to efficiently transmit infrared laser radiation while tolerating thermally-induced stresses and strains.

Type Ib diamonds (most synthetics) and polycrystalline diamond films manufactured by chemical vapor deposition (CVD), e.g., DIAFILM™ available from De Beers Industrial Diamond Division, Berkshire, England, may also be used.

Figure 5:
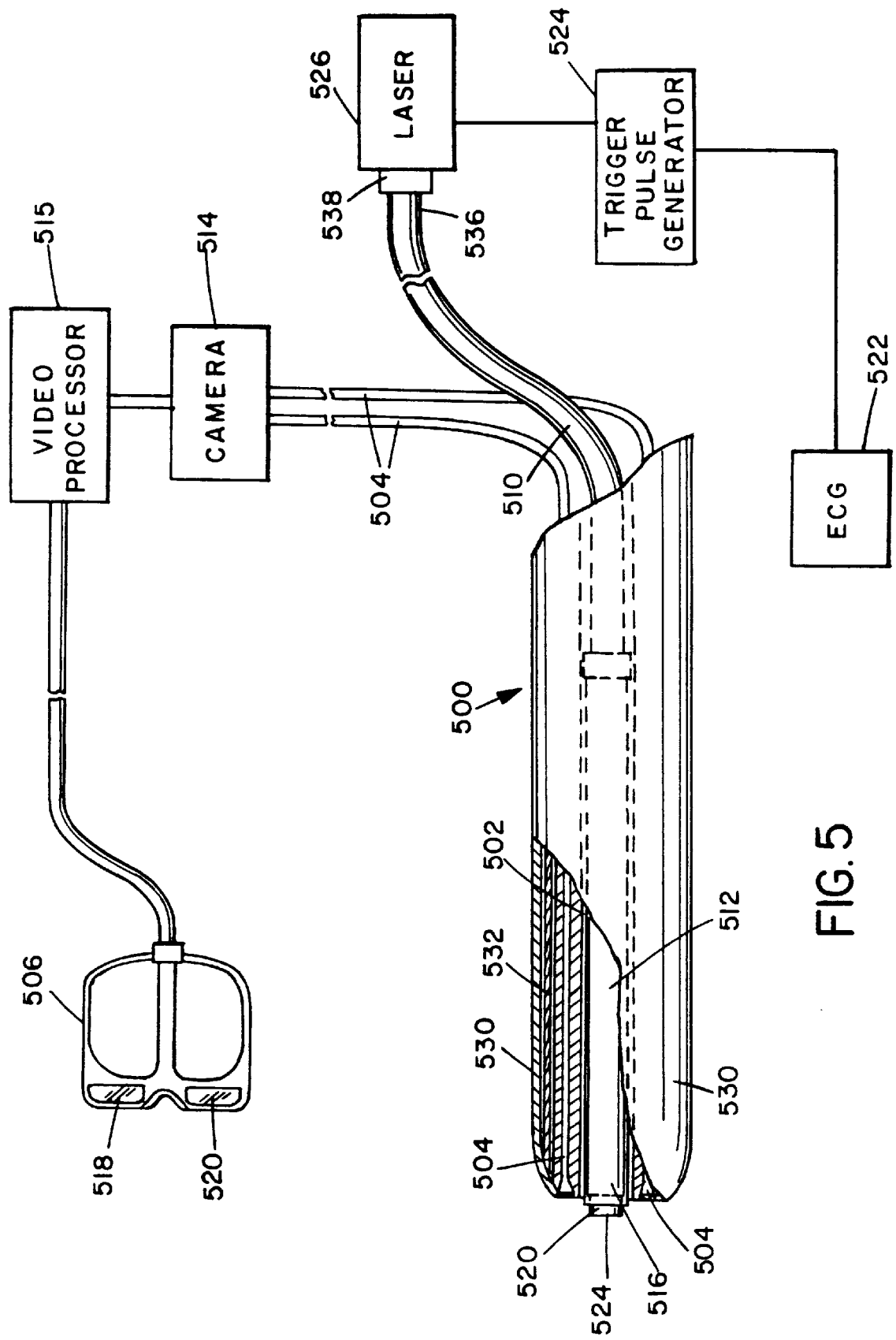
FIG. 5 is a diagrammatic view of the system for performing a TMR procedure.

The delivery system of the present invention be used in a TMR procedure for formation of channels in the myocardium. Such a system is illustrated in FIG. 5. The distal end 516 of hollow waveguide 512 is fitted with diamond tip 520 configured as a flattened or slightly curved lens at exit face 524. Hollow waveguide 512 is axially slidably retained within channel 502 of an endoscope 500 so that it may be extended from at least partially retracted into the housing 530. Housing 530 may also contain means for preforming one or more other functions in addition to retaining the waveguide 512 and diamond tip 520. At least a portion of flexible waveguide 510 is also retained within endoscope 500. The proximal end 536 of waveguide 510 is attached via connector 538 to laser 526.

In the preferred embodiment, housing 530 also retains within sheath 534 a plurality of axially-running control lines 532 which are attached at the distal end 502 for guiding the endoscope 500, as is known in the art, and a plurality of optical fibers 504, a first portion of which provide a source of visible illumination and a second portion of which provide visual feedback to the surgeon in the form of a three dimensional image. The three dimensional image, which is computer-enhanced using the images obtained via the optical fibers 504, is viewed using a binocular head mounted display 506 which is worn by the surgeon to provide real-time visual feedback in a minimally invasive surgical procedure. A three dimensional endoscope system is disclosed and described in International Patent Application Publication Number WO 94/28783 of American Surgical Technologies Corporation, the disclosure of which is incorporated herein by reference. One such commercial three-dimensional viewing system is available as the Vista Series 8000 Visualization and Information System, which incorporates the CardioScope™, for image acquisition, and CardioView™, for the head-mounted display, manufactured by Vista Medical Technologies, Vista Cardiothoracic Surgery Division, of Westborough, Mass.

Briefly, the three-dimensional image is produced by a conventional stereoscopic endoscope 500 which converts optical images of an object, in this case, the patient's heart, to left and right video image signals. Conversion of the two-dimensional optical images into left and right signals is achieved using a camera head 514 connected to a video processing module 516. After processing, the images are displayed on the left and right lenses 518,520 of the head mounted display 506. The lenses 518,520 may be liquid crystal displays (LCDs), such as described in U.S. Pat. No. 5,532,852 of Kalmanish, or may be passive displays as described in above-referenced International Publication No. WO 94/28783.

Visual monitoring of the procedure may be supplemented using known techniques of ultrasonic imaging by placing a ultrasonic probe within the patients esophogus. (See, e.g., I. Kupferwasser, et al., "Quantification of mitral valve stenosis by three-dimensional transesophageal echocardiography", Int'l J. Cardiac Imag., 12:241–247, 1996.)

Synchronization of the laser activation with the R waves of the electrocardiogram (ECG) signal utilizes a conventional ECG device 522 which is connected to a trigger pulse generating device 524. The trigger pulse is passed to a laser firing circuit which activates the laser 526 on the R wave of the electrocardiographic cycle, when the ventricle is maximally distended. An exemplary synchronization system is disclosed in U.S. Pat. No. 5,125,926 of Rudko, et al.

Referring to FIGS. 6a–6d, the method for performing a TMR procedure comprises making one or more small left anterior incisions (thoracotomies) through the fourth, fifth or sixth intercostal space to provide access to the left ventricle area of the heart 602. The distal end 604 of an endoscope 606 retaining flexible waveguide 607, hollow waveguide 608 and diamond tip 610 is inserted through and fed into incision 612 (indicated by dashed lines) until the tip 610 comes in contact with the pericardium 614. Endoscope 606 is configured such that it also retains the viewing optics, including illumination means, for providing a three-dimensional image for viewing using head-mounted display 616, which is described above with regard to FIG. 5. It also may include guidance means, such as control lines running axially along the length of the endoscope for manipulating the distal end 609 of the endoscope. Such guidance means are known in the art. Alternatively, the viewing optics may be housing within a separate endoscope which is inserted through a separate incision near incision 612.

Figure 6A:
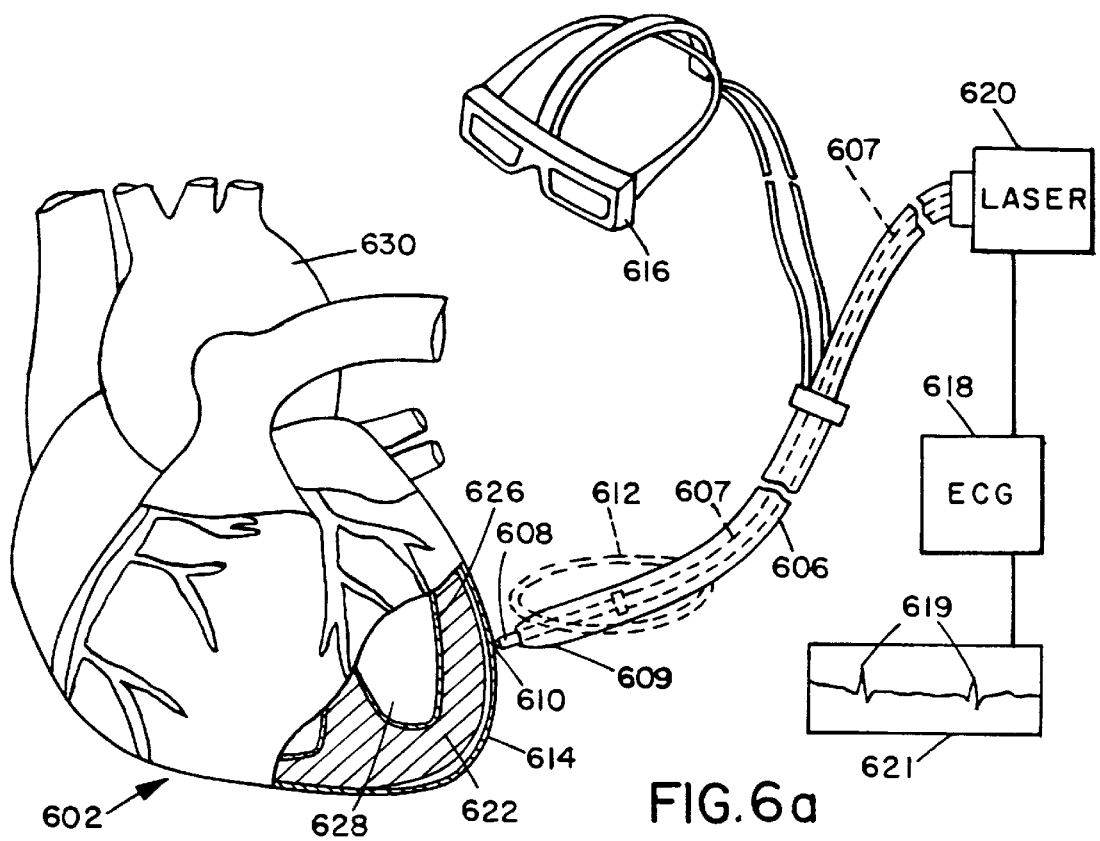
FIGS. 6a–6d are diagrammatic views of a human heart, partially cut away at the left ventricle, showing the steps of a TMR procedure, where

As illustrated in FIG. 6a, which shows the system set-up, the patient's ECG is monitored using an ECG device 618 which provides a trigger signal for activating $CO_2$ laser 620 in synchrony with the R wave 619, as indicated on ECG output display 621. Upon triggering, laser 620 emits a pulse of low power 10.6 micron laser light, i.e., less that 1000 W and preferably having a power within the range of 25–50 W, with a beam diameter of approximately 1 mm. (Generally, the laser should have a power density of greater than 5000 $W/cm^2$.)

Figure 6B:
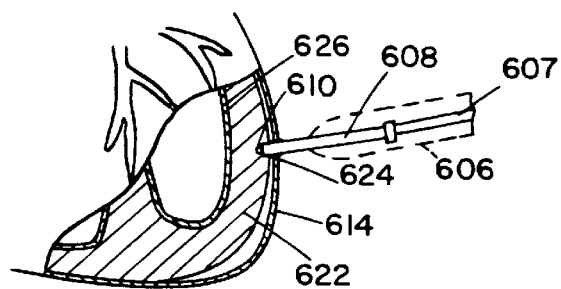
Figure 6C:
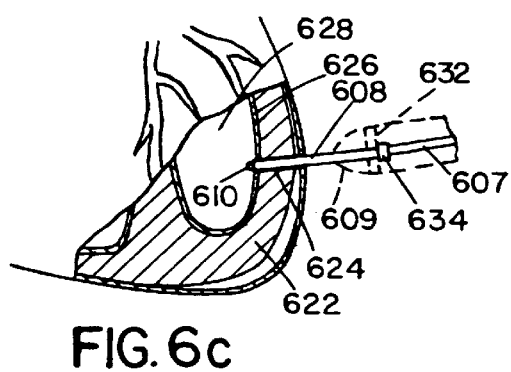

In FIG. 6b, which illustrates portions of both the heart 602 and overall system components, the distal end 607 of endoscope 606 is indicated by dashed lines to show the relative movement of the diamond tip 610 for advancing the tip into the heart tissue. It should be noted that, where the viewing and lasing components are housed in a common endoscope, distal end 607 is positioned to achieve the desired depth of view based upon the viewing optical components, since tip 610 can be advanced as needed relative to the distal end 607. The laser light emitted through diamond tip 610 in contact with the pericardium 614 ablates the tissue, providing a point of entry without tearing the pericardial tissue, and allows the tip 610 to be advanced into the myocardium 622. Triggered by detection of another R wave, the laser radiation ablates the myocardial tissue with which the tip 610 is in contact. As the myocardial channel 624 is formed, the tip 610 is advanced until the channel extends through the myocardium 622 and the endocardium 626 and, finally, the tip 610 extends into the left ventricle 628, as shown in FIG. 6c. In prior art TMR systems based on high power $CO_2$ lasers, "overshoot" after the channel is fully punched through the heart wall is controlled by blood contained within the left ventricle, since the water in the blood will absorb the radiation. However, such reliance may be risky and could result in damage to the opposite inner wall of the left ventricle. In the present method, since the ablation is advanced gradually, there is no "overshoot" with an uncontained high power laser beam. Stop 632, shown only in FIG. 6c, may be disposed within endoscope 606 to limit the travel of tip 610 by preventing flange 634 from advancing further, thus providing even greater control and accuracy in the application of the laser radiation. If such a stop is utilized, the length of hollow waveguide 608 should be sufficient to allow tip 610 to pass completely through the myocardium 622 and enter the left ventricle 628.

Figure 6D:
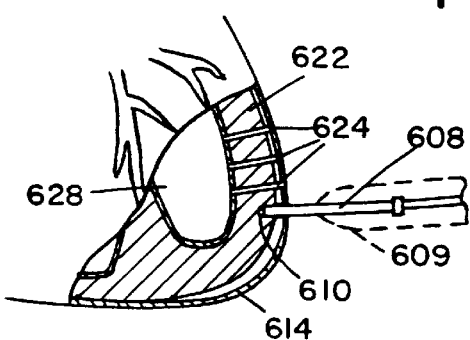

The tip 610 is then backed out through the channel 624 and another channel is begun at a different point on the outer wall of the left ventricle. FIG. 6d shows three completed channels 624 with another one in the process of being formed. As is known in the TMR art, a number of channels are formed, typically on the order of 15 to 40 channels, with diameters of about 1 mm, to provide the desired improvement in myocardial perfusion.

Since multiple applications of the laser radiation are required to create each channel, activation of the laser may be triggered by the R wave for every n beats, depending on the patient's heart rate. For example, for a rate of 60 beats/minute, n might be selected to be 5, 10, or some other integer value. Consideration may also need to be given to how long the laser requires between pulses, with the triggering rate being set to a value corresponding to a period equaling an integer times the heart rate which is greater than the laser recharge cycle.

The pericardium 614 may provide a relatively high amount of initial resistance due to its density. Therefore, as an alternative to the flat or slightly rounded tip, it may be desirable to utilize a lance or spear-type diamond tip, such as that illustrated in FIG. 3b, to facilitate perforation of the pericardial tissue. The pericardium 614 heals almost immediately, as indicated in FIG. 6d, while the channels in the myocardium remain patent.

Variations in the TMR procedure with the inventive system can occur based upon the method of obtaining access to the myocardium. In one alternative method, the heart is accessed through catheters placed in the patient's femoral artery and passed through the aorta 630, which can be seen in FIG. 6a, across the aortic valve and into the left ventricle 628. Using this method, perforation of the pericardium 614 is not required, and the channels are created in the myocardium 622 to a pre-determined depth. In another alternative method, access is gained in an open chest procedure via a sternotomy or thoracotomy. As in the first method, the diamond tip is initially placed in contact with the pericardium 614, and the channels are formed completely through the myocardium 622.

Because the $CO_2$ laser radiation is delivered by contacting the tissue, the optical components of the system can be simplified as compared to conventional $CO_2$ laser-based TMR systems, which require an additional laser, typically helium-neon (He-Ne), which emits a visible red light (632.8 nm), with corresponding optics, for aiming purposes. In the present invention, contact, and thus, aiming, is readily monitored using the images generated by the 3-D endoscope 606 and viewer 616. As previously mentioned, esophageal ultrasonic imaging may also be used to monitor the positioning of the device and the progress of the procedure.

An important advantage of the present invention is that, because of its low power requirements, it may be used with virtually any $CO_2$ laser head, including retrofitting of a $CO_2$ laser which may already be available within the hospital. This provides greater access to TMR capability for hospitals which may not have the budget for purchasing dedicated TMR systems, which systems cost well over $100,000, and makes it possible to perform the procedures more cost effectively. The contact procedure allows the power level to be significantly lower than that required for non-contact $CO_2$ laser-based systems, which require power levels of 800 W and up in order to supply sufficient energy to create a complete channel in a single pulse. (A non-contact TMR system must create the channel in a single pulse since exact positioning of a subsequent pulse at the same point may be difficult on the beating heart.) The contact delivery system of the present invention allows for greater precision and improved safety, while providing a more economical means for performing TMR procedures.

In an alternate embodiment, the laser delivery system of the present invention may be used to perform a partial left ventriculectomy (PLV), also known as the Batista procedure, for treatment of severe dilated cardiomyopathy. The same low power $CO_2$ laser may be used as that used for the TMR procedures. Other types of lasers, such as Ho:YAG or Nd:YAG may be used, however, the advantages of cost savings with the low power $CO_2$ laser may not be available. The diamond tip used for the delivery system will have at least one cutting edge, and may be any of the configurations shown in FIGS. 3a–3d, or variations thereupon.

The method of performing a PLV using the inventive system comprises providing access to the heart by way of a sternotomy or thoracotomy. It may be preferred to utilize recently reported systems and procedures for minimally invasive surgery, such as the system developed by Cardio Thoracic Systems, Inc. of Cupertino, Calif. under the trademark MIDCAB™. Such systems permit access to the heart through an incision through one of the left intercostal spaces. Spreaders are used to increase the spacing between a pair of ribs to provide a window to the heart.

Figure 7A:
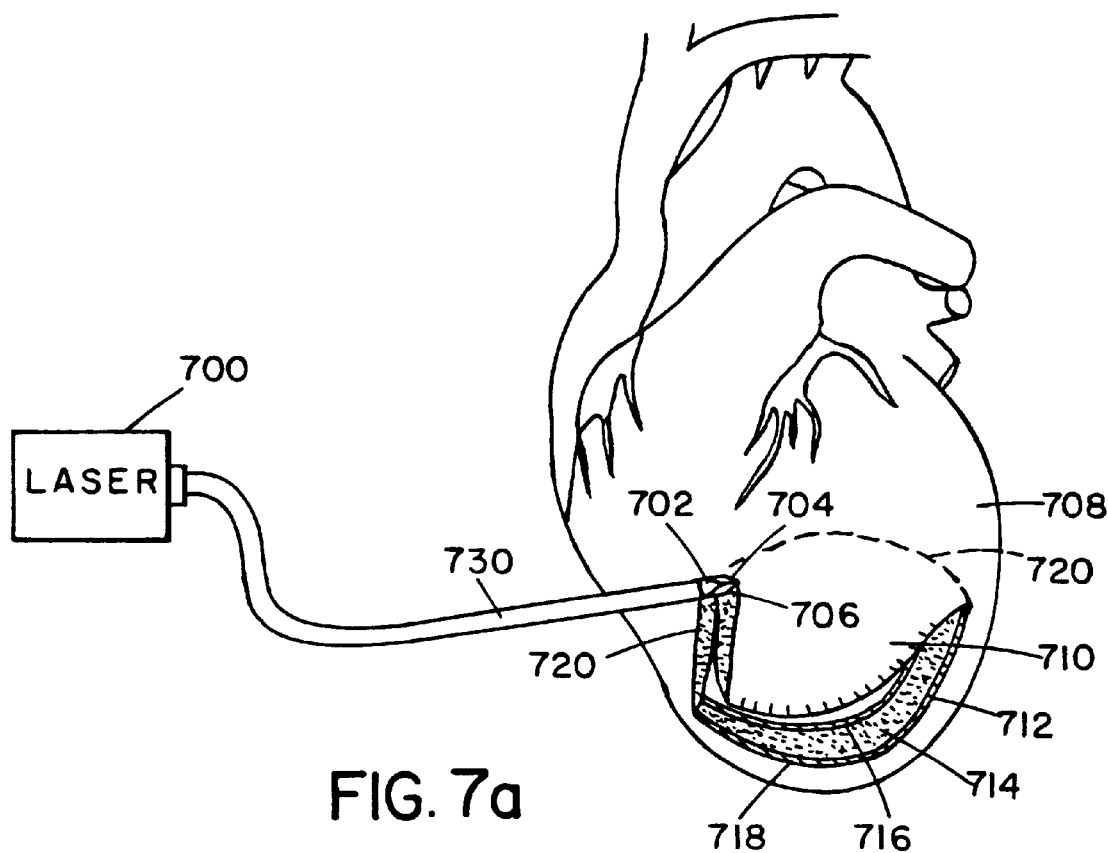
FIGS. 7a and 7b are diagrammatic views of a human heart showing the steps of a PLV procedure, where
Figure 7B:
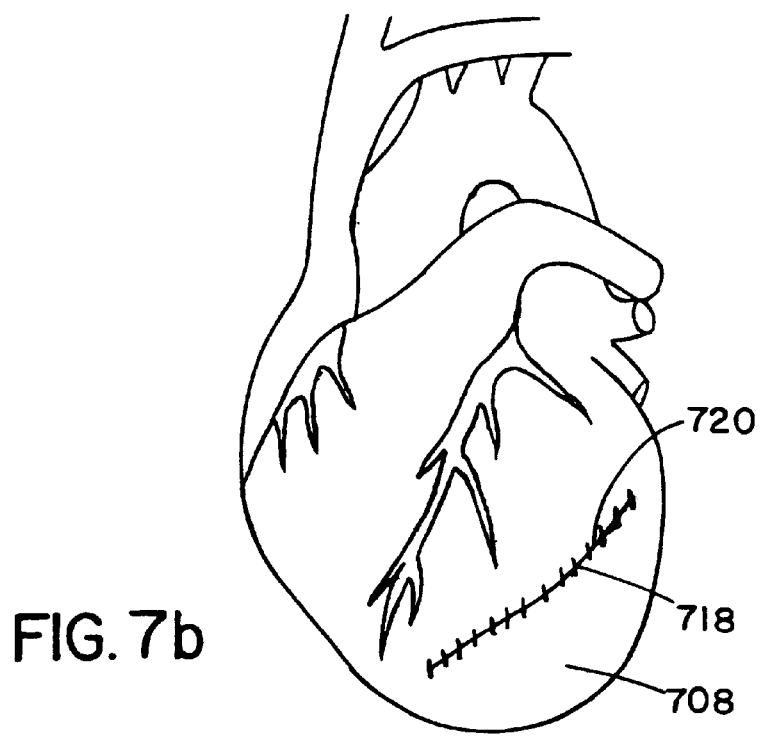

The patient is placed on a heart-lung bypass machine. The heart continues beating in order to permit identification of the area to be removed. As illustrated in FIG. 7a, using the inventive laser delivery system with a low power $CO_2$ laser 700, typically on the order of 25–50 W, the diamond tip 702, shown here with two beveled edges 704,706, is retained within hollow waveguide 730 and is used to simultaneously cut and irradiate tissue in the wall of the left ventricle 708 between the papillary muscles (not shown) to remove a wedge of tissue 710. The laser radiation is emitted through edges 704,706 to facilitate cutting, particularly through the pericardium 712, and to induce photocoagulation of the tissue as the incision is made through the myocardium 714 and endocardium 716 thus reducing bleeding. The stippling at the incision through the myocardium 714 is provided to indicate photocoagulated tissue. The dotted line indicates the intended line of incision 720. After the wedge of tissue 710 is removed, the edges 718, 720 of the incision are pulled together and sutured to form a smaller left ventricle, as shown in FIG. 7b, with thicker walls. The stippling at the joined incision again indicates photocoagulated tissue of the pericardium 712. The patient's heart is restarted, the heart-lung machine is removed, and the thoracic incision is closed.

Other types of lasers may be substituted for the low power $CO_2$ laser in this procedure in order to provide photocoagulation of the tissue as the incision is made mechanically with the diamond blade. Alternative lasers include Ho:YAG, Nd:YAG, and solid state, all emitting within the IR range. Other lasers are known for their photocoagulation capabilities including argon and excimer.

The laser delivery system of the present invention provides several advantages over current PLV techniques. These advantages includes reduced tearing of the heart tissue resulting from conventional steel blade knives or surgical scissors, since the diamond blade has a much cleaner, sharper edge, which produces less cell damage, and the laser radiation augments the mechanical cutting with ablation, at least with the $CO_2$ laser, and induces photocoagulation to reduce bleeding as the cut is made with the $CO_2$ laser as well as many other types of laser. These advantages, in turn, reduce the time in surgery and the risk of post-operative bleeding, and contribute to faster healing.

Figure 8A:
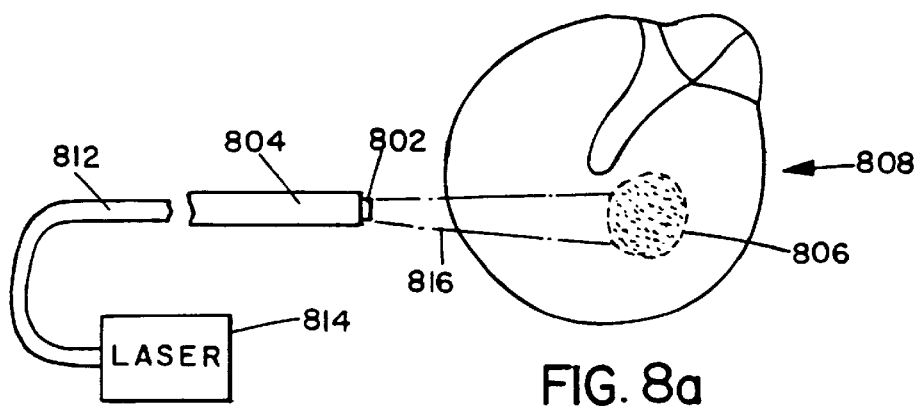
FIGS. 8a and 8b are diagrammatic views of a tympanic membrane, where
Figure 8B:
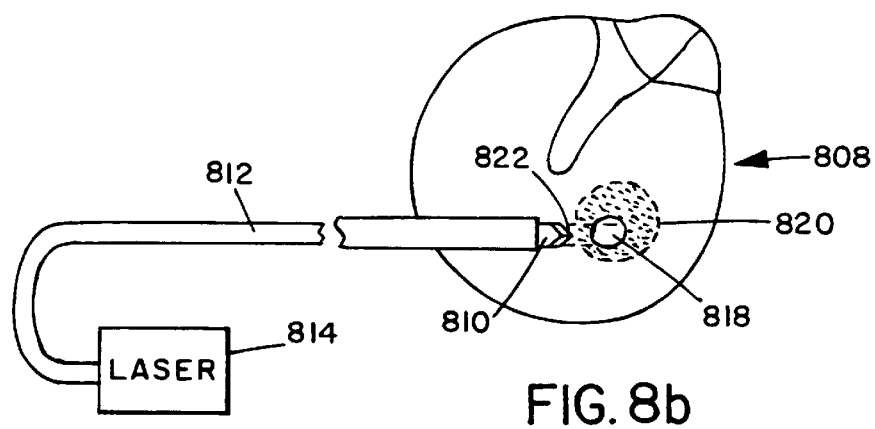

A third embodiment of the inventive laser delivery system may be used for performing a myringotomy for treatment of otitis media. In this case, two different diamond tips may be used. The first diamond tip 802 mounted within hollow waveguide 804, shown in FIG. 8a, is configured as an expanding lens which slightly enlarges the diameter of beam 816 from a low power $CO_2$ laser 814, e.g., 25–50 W, to irradiate an area 806 on the tympanic membrane 808, preferably, but non-necessarily non-contact (for the patient's comfort), resulting in the denaturing of the tissue in the area 806. The denaturing is indicated by stippling. A hollow waveguide with a second diamond tip 810, shown in FIG. 8b, is then attached at the distal end of the waveguide 812 connected to the $CO_2$ laser 814 to complete the procedure. Second diamond tip 810 may be configured as a focusing lens, a flat window, or a lance-type blade as shown. The key to second diamond tip 810 is that it generates a narrower, more focused beam than that delivered by first diamond tip 802 so that a smaller area of impact is defined on the tympanic membrane 808 with a higher power density. The smaller, diameter, higher power density beam is then used to ablate a small perforation 818 generally at the center of the area of the denatured tissue 806 so that a rim 820 of denatured tissue remains around the perforation. This latter aspect of the procedure is preferably performed in two steps. The first step is that a small "vent" hole is formed to release any pressure that has built up behind the tympanic membrane which could otherwise lead to bursting of the membrane if it were suddenly perforated. After the pressure has been equalized, a larger perforation is formed to provide the desired drainage. The small vent hole may be created by gently pushing the tip 822 of the lance blade 810 against the membrane, then backing the blade away from the tissue to allow the pressure release. The desired, larger perforation 816 can then be created by a combination of mechanical pressure from the blade 810 and the laser ablation, or by either alone.

The rim of denatured tissue 820 retards the healing of the perforation, giving it extended patency. This eliminates the need for placement of a shunt for drainage such as is required in most current myringotomy procedures.

Figure 9:
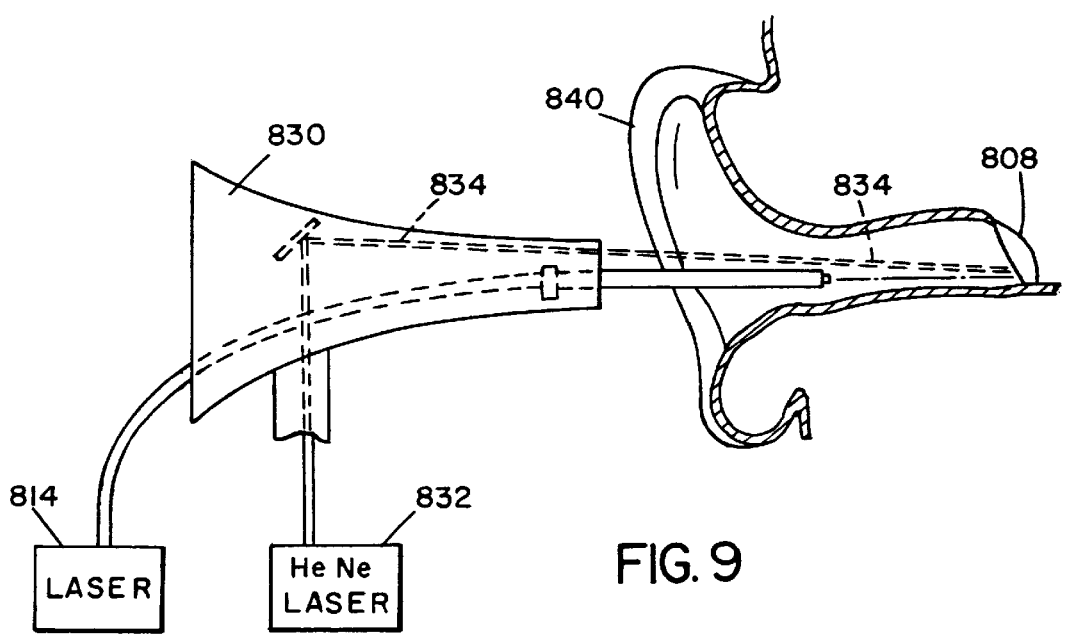
FIG. 9 is a diagrammatic view of a partial cross-section of a human ear and an otoscope adapted for performing a myringotomy according to the present invention.

Observation and control of the myringotomy procedure using the inventive system may be achieved using conventional viewing optics including an otoscope 830 with an illumination source 832, illustrated in FIG. 9 along with a section of an ear 840. Illumination source 832 may double as the targeting means, and, in this case, is shown as a He-Ne laser along with the appropriate optics for directing the beam 834 from the He-Ne laser 832 along substantially the same optical path as, or to convergence with, the ablation laser 814.

The myringotomy procedure is not limited to the wavelength emitted by a $CO_2$ laser, and a wide range of laser wavelengths may be used, including lasers emitting in the near- and mid-IR, including Ho:YAG, and near-UV ranges, such as excimer. The only requirement is that the laser radiation must be sufficient for achieve adequate denaturing of the tissue as required for extended patency of the perforation.

The described myringotomy procedure takes advantage of the benefits of laser ablation and other laser/tissue interactions without requiring the complex optical systems taught by others in the art. For example, U.S. Pat. No. 5,280,378 of Lombardo describes a cyclically scanned laser for use in myringotomy procedures. The scanned beam forms many tiny holes in the tympanic membrane to outline an area which can then be punched through at the perforations. In that procedure, the laser is used only for cutting/piercing, and no intentional denaturing occurs. Thus, the patency of the perforation is not improved significantly relative to mechanical lancing procedures and a shunt will still be required.

The laser delivery system of the present invention provides means for precise control of surgical lasers, especially $CO_2$ lasers, allowing the safe usage of inexpensive conventional lasers for advanced laser surgical techniques. The delivery system allows hospitals and physicians to avoid the significant expense involved in purchasing new, dedicated laser surgical systems when they already have access to $CO_2$ lasers which were part of an older and possibly out-of-date surgical system. The combined laser and mechanical surgical techniques which are enabled by the low power levels allow surgeons to exploit the benefits of each technique without compromise, providing significant advantages over prior art laser systems, particularly for transmyocardial revascularization and myringotomy procedures. Further, the disclosed invention introduces the use of laser techniques for use in partial left ventriculectomy procedures and similar cardiac surgeries. Other surgical procedures not specifically mentioned will similarly benefit from the improvements disclosed herein relating to laser delivery.

It will be apparent to those skilled in the art that various modifications and variations can be made in the system and method of the present invention without departing from the spirit or scope of the invention. Thus, it is intended that the present invention cover the modification and variations of this invention provided they come within the scope of the appended claims and their equivalents.

I claim:

1. A surgical laser delivery system for delivering laser radiation for performing surgery on a biological tissue, the system comprising:

a laser having an output for emitting the laser radiation at a wavelength and a power level adapted for ablation of the biological tissue;

a flexible waveguide having a first proximal end, a first distal end and a first length, the proximal end attached to the output of the laser;

a rigid waveguide formed from a hollow metal tube having a polished interior surface, the rigid waveguide having a second proximal end connected to the first distal end of the flexible waveguide, a second distal end, a second length much less than the first length, and an interior cross-sectional area;

a diamond tip having a base end with an entrance face, at least one sidewall, and a tip end with at least one exit face, the base end having an exterior cross-sectional area to closely fit within the interior cross-sectional area of the second distal end of the rigid waveguide so that the tip end extends from the rigid waveguide, the at least one sidewall having a surface for internal reflection of laser radiation within the diamond tip, wherein substantially all of the laser radiation is emitted through the at least one exit face and wherein the tip end is adapted for contacting the biological tissue for application of the laser radiation thereto.

2. A surgical laser delivery system as in claim 1, wherein the diamond tip is formed as a window with the entrance face and exit face parallel to each other.

3. A surgical laser delivery system as in claim 1, wherein the diamond tip is formed as a lens with the exit face having a curved surface.

4. A surgical laser delivery system as in claim 1, wherein the diamond tip is formed as a blade having at least one beveled edge adapted for mechanical cutting of the biological tissue.

5. A surgical laser delivery system as in claim 4, wherein the blade has two beveled edges which intersect to form a pointed apex for piercing the biological tissue.

6. A surgical laser delivery system as in claim 1, wherein the entrance face of the diamond tip has an anti-reflective film formed thereon.

7. A surgical laser delivery system as in claim 1, wherein the rigid waveguide is formed from stainless steel.

8. A surgical laser delivery system as in claim 1, wherein the second distal end of the rigid waveguide is crimped around the base of the diamond tip.

9. A surgical laser delivery system as in claim 1, wherein the laser is a $CO_2$ laser and the power level is less than 1000 Watts.

10. A surgical laser delivery system as in claim 9, wherein the power level is less than 100 Watts and the laser radiation has a power density of greater than 5000 Watts/cm$^2$.

11. A surgical laser delivery system as in claim 10, wherein the power level is within the range of 25–50 Watts.

12. A surgical laser delivery system as in claim 1, wherein the at least one sidewall of the diamond tip has a surface adapted for internal reflection of the laser radiation.

13. A surgical laser delivery system as in claim 1, wherein the rigid waveguide and at least a portion of the flexible waveguide are disposed within an endoscope.

14. A surgical laser delivery system as in claim 13, wherein the endoscope includes viewing optics, and further comprising a three-dimensional image processor and a display means for providing visual feedback to a surgeon.

15. A method for performing a laser surgical procedure using a low power $CO_2$ laser for ablation of biological tissue, the method comprising:

providing a flexible waveguide for connection to the $CO_2$ laser at a first end for directing laser radiation;

providing at least one diamond tip retained within a rigid hollow waveguide, the diamond tip having a tip end with at least one exit face, wherein the tip end is selected according to the laser surgical procedure to be performed;

placing the tip end in contact with the biological tissue;

activating the $CO_2$ laser to ablate the biological tissue in contact with the tip end;

advancing the tip end through the biological tissue as the tissue is ablated until a pre-determined amount of tissue has been ablated.

16. The method of claim 15, wherein the biological tissue is a heart and the laser surgical procedure is transmyocardial revascularization.

17. The method of claim 16, wherein the step of activating the $CO_2$ laser includes pulsing the $CO_2$ laser in response to a trigger signal.

18. The method of claim 17, wherein the trigger signal is activated in response to a pre-determined component wave of an electrocardiogram of the heart.

19. The method of claim 16, wherein the at least one tip exit face is flat.

20. The method of claim 15, wherein the biological tissue is a heart and the laser surgical procedure is a partial left ventriculectomy, and wherein the at least one exit face has a beveled edge.

21. The method of claim 20, wherein the step of advancing the tip end comprises mechanically cutting the biological tissue with the beveled edge while simultaneously applying laser radiation to induce photocoagulation.

22. The method of claim 21, wherein the diamond tip has two exit faces comprising a pair of beveled edges disposed to form an apex point for piercing.

23. The method of claim 15, wherein the biological tissue is a tympanic membrane and the laser surgical procedure is a myringotomy, wherein the at least one diamond tip comprises a first diamond tip for irradiating and denaturing an area of the tympanic membrane and a second diamond tip for ablating a perforation in the denatured area.

24. The method of claim 23, wherein the second diamond tip has two beveled edges and an apex point for piercing the denatured area.

* * * * *